United States Patent

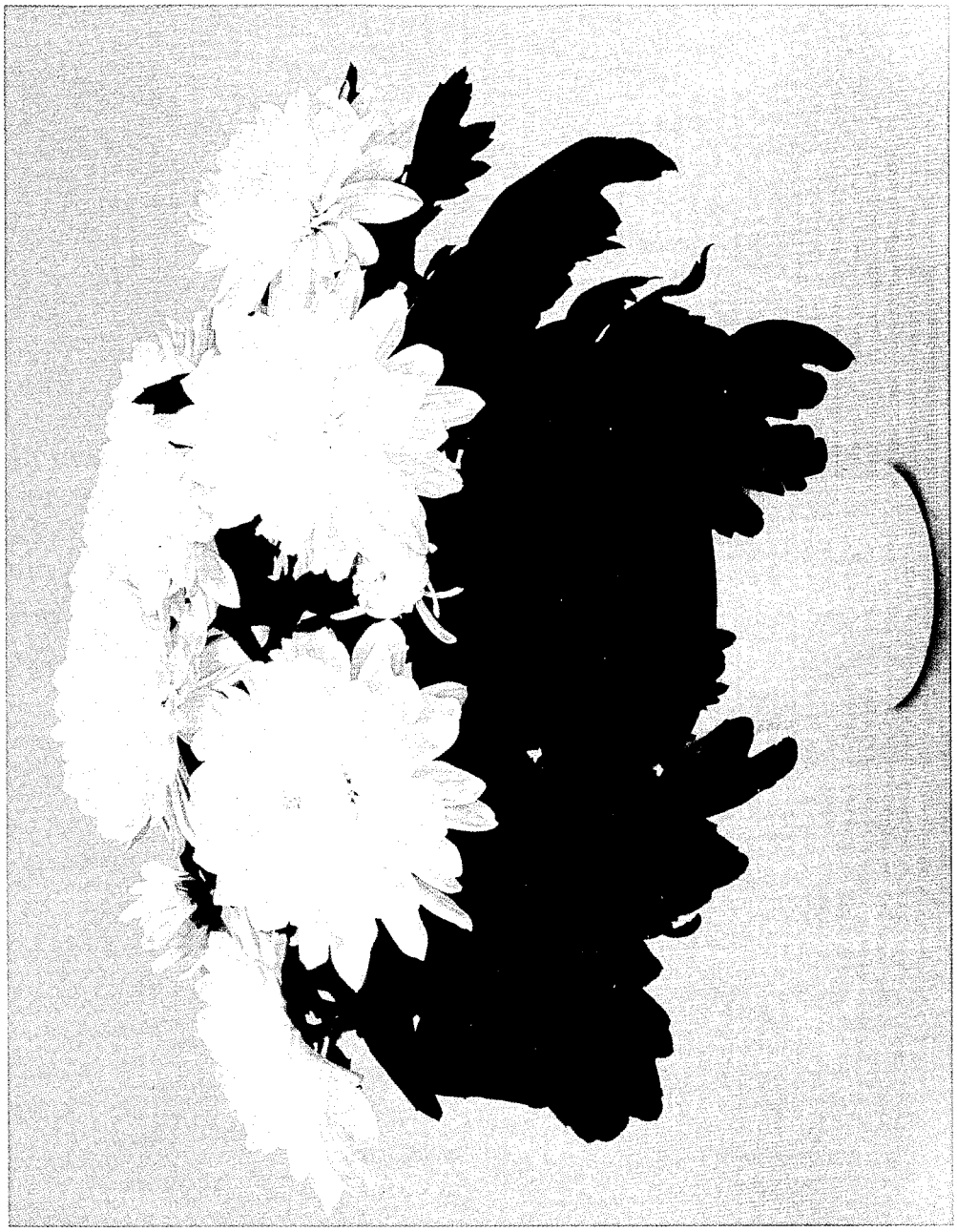

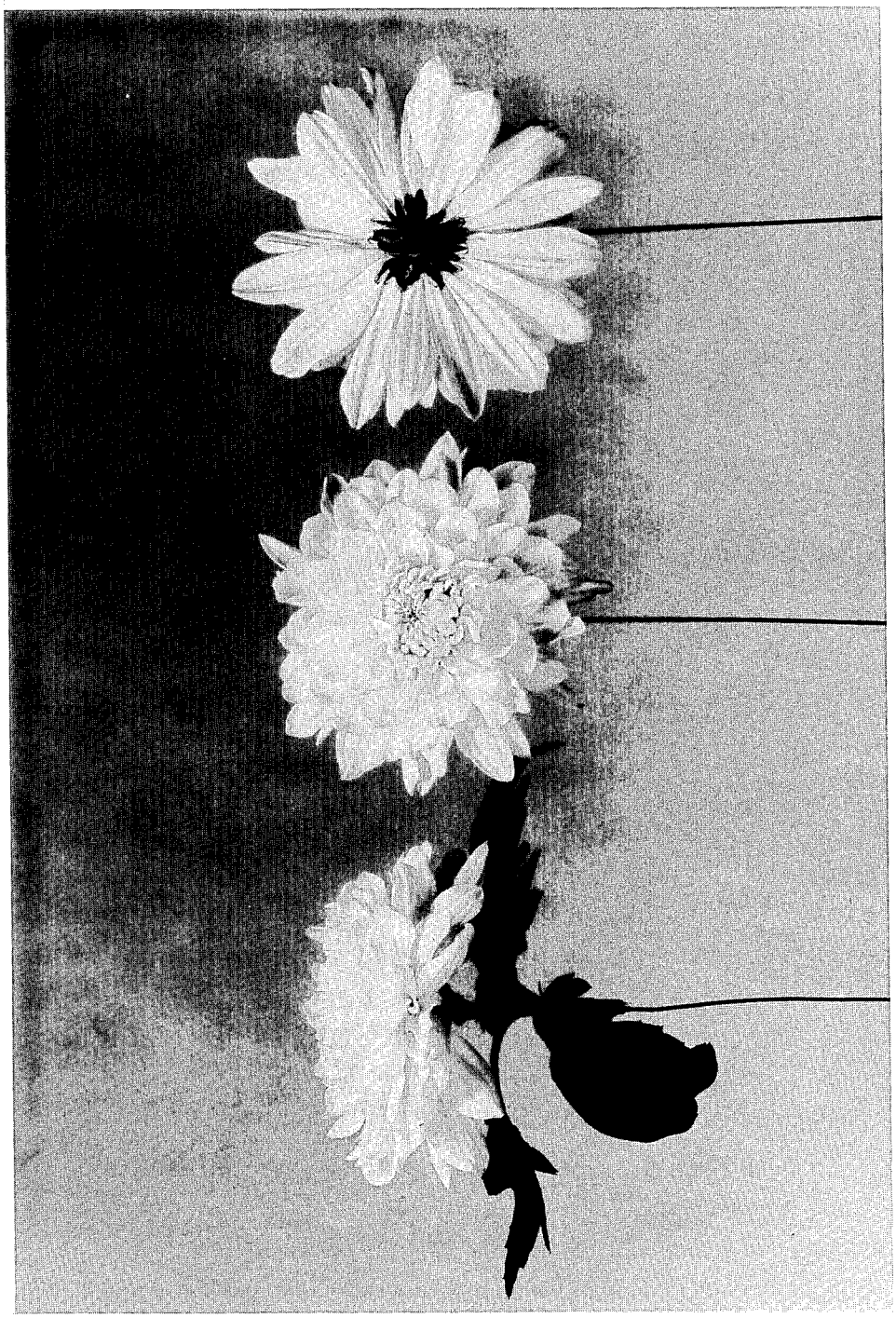

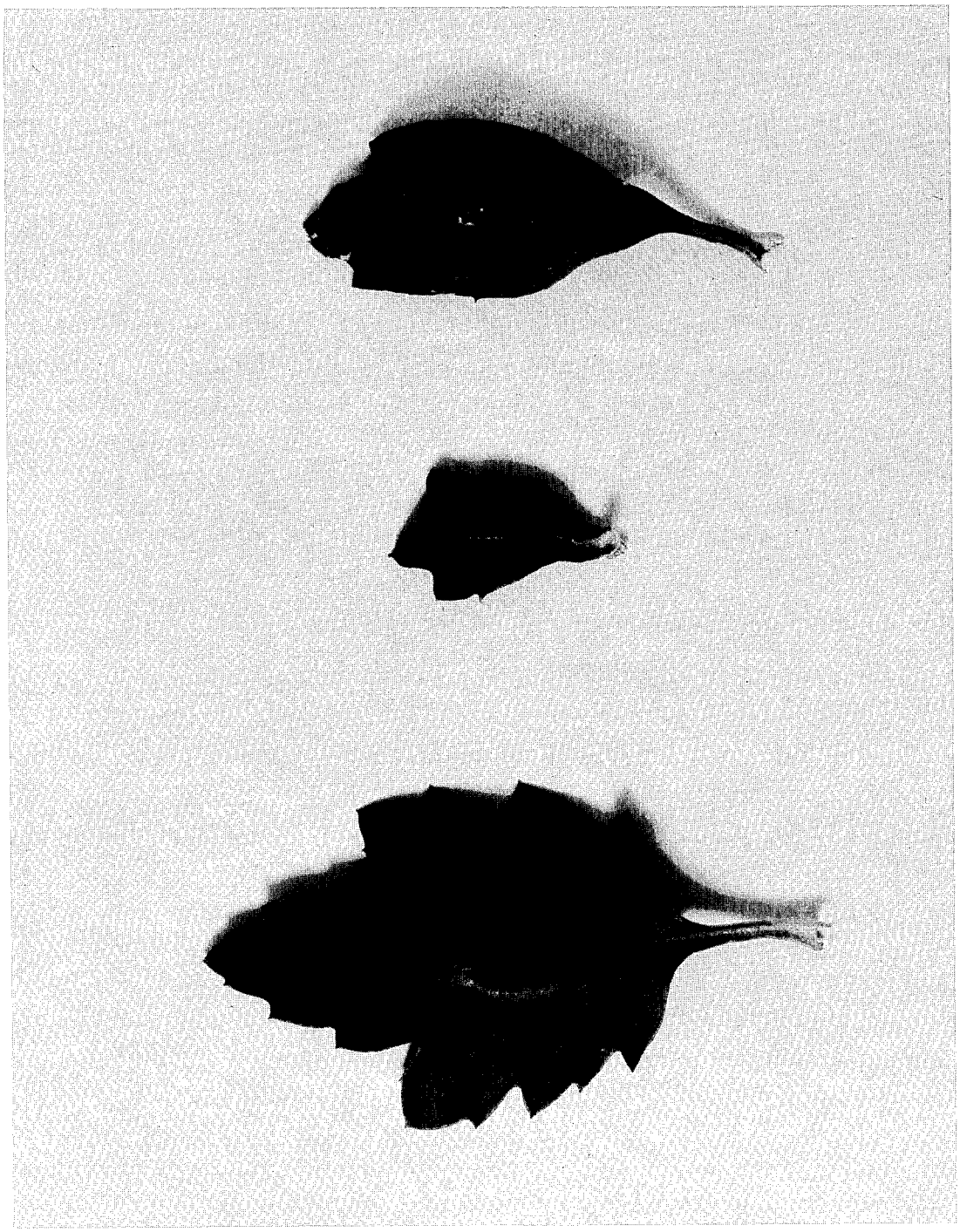

Plant Pat. 3,907
Patented June 15, 1976

3,907
CHRYSANTHEMUM PLANT

Walter H. Jessel, Jr., Doylestown, and William E. Duffett, Akron, Ohio, assignors to Yoder Brothers, Inc., Barberton, Ohio Filed May 15, 1975, Ser. No. 577,892
Int. Cl. A01h *5/00*
U.S. Cl. Plt.—78 1 Claim

The present invention comprises a new and distinct cultivar of *Chrysanthemum morifolium*, Ramat., hereinafter referred to by the cultivar name Intrepid Gold (#68146D01).

Intrepid Gold is an induced sport of Intrepid White (#68146001), disclosed in our pending U.S. application Ser. No. 577,921, filed May 15, 1975. Intrepid Gold was discovered and selected by William E. Duffett and Walter H. Jessel, Jr. on June 26, 1973 as one branch of one plant within a flowering block of Intrepid White in a controlled environment in Barberton, Ohio. Plants within the flowering block were derived from stock plants which had been irradiated as rooted cuttings with an X-ray source of 1800 r units.

Intrepid White, an ivory white decorative, was originated by the present inventors in 1968 as a product of a controlled breeding program. The female, or seed parent was #65307001 (unnamed seedling), a light pink decorative originated by the present inventors from a cross between Princess Anne (#21560E02; unpatented; commercially available) and Orchid King (#21555001; unpatened; commercially available). The male, or pollen parent of Intrepid White, was Mandalay (#61865001; unpatented; commercially available). The male, or pollen originated by the present inventors from a cross between Woking Scarlet (#21383001; unpatented; commercially available) and Mayford Crimson (#21402001; unpatented; commercially available).

Intrepid Gold is a product of a planned sport induction program which had the objective of expanding the color range of Intrepid White. Intrepid White was a product of a planned breeding program which had the objective of creating medium to large sized decoratives for pot mum culture with uniform nine and ten week flowering response and the ability to produce commercially acceptable quality in controlled flowering programs on a year round basis.

The first act of asexual reproduction of Intrepid Gold was accomplished when vegetative cuttings were taken from the initial selection in January 1973 in a controlled environment in Barberton, Ohio by a technician under formulations established and supervised by William E. Duffett and Walter H. Jessel, Jr. Horticultural examination of selected units initiated Dec. 1, 1973 has demonstrated that the combination of characteristics as herein disclosed for Intrepid Gold are firmly fixed and are retained through successive generations of asexual reproduction.

Intrepid Gold has not been observed under all possible environments. The phenotype may vary significantly with variations in environment such as temperature, light intensity, and daylength. The following observations, measurements, and comparisons describe pinched, disbudded plants grown in a greenhouse in Barberton, Ohio under environmental conditions which closely approximate those generally used in commercial practice, as described in Chart A and Chart B which appear at the end of the present specification.

The following traits have been repeatedly observed and are determined to be basic characteristics of Intrepid Gold which in combination distinguish this chrysanthemum as a new and distinct cultivar:

(1) Decorative inflorescence type.

(2) Semi-incurved inflorescence form not known to reflex.

(3) Diameter across face of inflorescence from 4.0 to 5.5 inches at maturity.

(4) Golden yellow ray floret color devoid of bronze tinging.

(5) Uniform eight week flowering response.

(6) Short plant height.

(7) Semi-upright branching habit.

(8) Adaptability to a wide range of container sizes due to responsiveness to day length and B–9.

The accompanying photographic drawings show typical inflorescence and foliage characteristics of Intrepid Gold with colors being as nearly true as possible with illustrations of this type. Sheet 1 is a color photograph of Intrepid Gold. Sheet 2 is a black and white photograph showing three different views of the inflorescence of Intrepid Gold. Sheet 3 is a black and white photograph showing the foliage of Intrepid Gold at three stages of growth.

Of the many commercial cultivars known to the present inventors, the most similar existing cultivar in comparison to Intrepid Gold is Bright Golden Anne (#2156DE02; unpatended). Intrepid Gold may also be compared to the parental cultivar, Intrepid White. Reference is made to attached Chart C which compares certain characteristics of Bright Golden Anne and Intrepid White with the same characteristics of Intrepid Gold. General comparisons are as follows:

In comparison to Bright Golden Anne, Intrepid Gold has a shorter height, a golden yellow color devoid of bronze tinging, a smaller diameter across face of inflorescence and a shorter flowering response period. The branching habit, inflorescence form, and inflorescence type of Intrepid Gold are similar to those of Bright Golden Anne.

In comparison to Intrepid White, Intrepid Gold has a different inflorescence color and different inflorescence form. The branching habit, diameter across the face of inflorescence height, flowering response period, and inflorescence type of Intrepid Gold are similar to those of Intrepid White.

In the following description, color references are made to The Munsell Limit Color Cascade, 1972 edition. The color values were determined between 8:30 a.m. and 9:30 a.m. on February 6, 1975 under 140 foot candle light intensity at Barberton, Ohio.

BOTANICAL CLASSIFICATION

*Chrysanthemum morifolium,* Ramat., cv Intrepid Gold

(I) *Inflorescence*

(A) Capitulum:

*Form.*—Semi-incurved.

*Type.*—Decorative.

*Permanence.*—14–18 days.

*Diameter across face.*—4.0 to 5.5 inches.

(B) Corolla of ray florets:

*Texture (adaxial).*—Glabrous.

*Appearance and form.*—Ligulate.

*Arrangement.*—Whorled on receptacle.

*Persistence.*—Resists shatter.

*Color (abaxial).*—26–6 to 26–3.

*Color (adaxial).*—25–6 (apex) to 26–3.

(C) Reproductive organs:

*Androecium.*—Present disc florets only; syngenesious stigma; scant pollen.

*Gynoecium.*—Present both ray and disc florets; inferior bicarpellate ovary; single style; 2-lobed stigma.

(II) *Plant*

(A) General appearance: Semi-upright; short.

(B) Duration and texture: Perennial; herbaceous.

(C) Foliage:

*Color (abaxial).*—Approximately 20–15 to 20–13.

*Color (adaxial).*—Approximately 20–13.

*Shape.*—Spatulate; moderately lobed.

*Texture.*—Glabrous.

*Veination.*—Prominent.

*Margin.*—Slightly serrated.

CHART A—AVERAGE GREENHOUSE CHRYSANTHEMUM ENVIRONMENTS USED FOR BARBERTON, OHIO

| Season | Temperatures used (°F.) Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: on, 5:30 p.m.; off, 7:30 a.m. | From Oct. 15: 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15: 300 p.p.m. |
| Summer | 62 to 68 | 70 to 90 | 65 to 75 | 1 to 2 weeks at 3 hours per night of 7–10 f.c. | On, 6:00 p.m.; off, 8:00 a.m. | None. |

NOTE.—For intensity of direct solar radiation, refer to Chart B.

CHART B

INTENSITY OF DIRECT SOLAR RADIATION

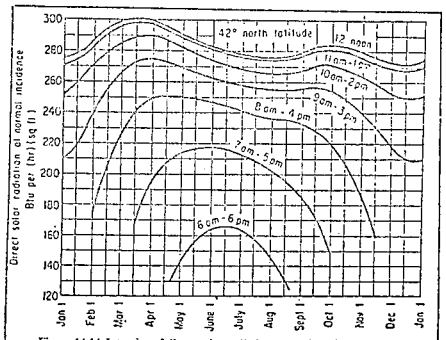

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF INTREPID GOLD WITH BRIGHT GOLDEN ANNE AND INTREPID WHITE

| Cultivar | Inflorescence color | Diameter across face of inflorescense (inches) | Height | Branching habit | Flowering response period | Inflorescence form and type |
|---|---|---|---|---|---|---|
| Intrepid Gold | Golden yellow | 4.0 to 5.5 | Short | Semi-upright | 8 | Semi-incurved decorative. |
| Bright Golden Anne | do | 5.0 to 5.75 | Very tall | do | 10 | Do. |
| Intrepid White | Ivory to white | 4.0 to 5.5 | Short | do | 8 | Flat decorative. |

NOTE.—Comparisons made of plants grown in a greenhouse in Barberton, Ohio under conditions as defined in Chart A and Chart B.

We claim:

1. A new and distinct cultivar of chrysanthemum plant particularly characterized as to uniqueness by the combined characteristics of decorative inflorescence type, semi-incurved inflorescence form not known to reflex, diameter across face of inflorescence from 4.0 to 5.5 inches at maturity, golden yellow ray floret color devoid of bronze tinging, uniform eight week flowering response, short plant height, semi-upright branching habit, and by its adaptability to a wide range of container sizes due to responsiveness of height to day length and B–9.

No references cited.

ROBERT E. BAGWILL, Primary Examiner